United States Patent [19]
Baindur et al.

[11] Patent Number: 5,891,737
[45] Date of Patent: Apr. 6, 1999

[54] COMBINATORIAL NON-PEPTIDE LIBRARIES

[75] Inventors: Nand Baindur, Edmonds; Virender M. Labroo, Mill Creek, both of Wash.

[73] Assignee: ZymoGenetics, Inc., Seattle, Wash.

[21] Appl. No.: 482,231

[22] Filed: Jun. 7, 1995

[51] Int. Cl.[6] .................................................. G01N 33/543
[52] U.S. Cl. ..................... 436/518; 548/400; 548/556; 546/298
[58] Field of Search ............................... 514/15; 530/328, 530/300; 436/518; 548/400, 556; 546/298

[56] References Cited

U.S. PATENT DOCUMENTS

| | | | |
|---|---|---|---|
| 5,182,366 | 1/1993 | Huebner et al. | 530/334 |
| 5,266,684 | 11/1993 | Rutter et al. | 530/334 |
| 5,382,513 | 1/1995 | Lam et al. | 435/7.1 |
| 5,385,889 | 1/1995 | Kyle et al. | 514/15 |

OTHER PUBLICATIONS

Kerr et al., *J. Am. Chem. Soc. 115*: 2529–2531, 1993.
Patek et al., *Tetrahedron Letters 36(13)*: 2227–2230, 1995.
Kick et al., *J. Med. Chem. 38*: 1427–1430, 1995.
Erb et al., *Proc. Natl. Acad. Sci. USA 91*: 11422–11426, 1994.
Simon et al., *Proc. Natl. Acad. Sci. USA 89*: 9367–9371, 1992.
Lebl et al., *Techniques in Protein Chemistry V*: 541–548, 1994.
Needels et al., *Proc. Natl. Acad. Sci. USA 90*: 10700–10704, 1993.
DeWitt et al., *Proc. Natl. Acad. Sci. USA 90*: 6909–6913, 1993.
Hirschmann et al., *J. Am. Chem. Soc. 114*: 9217–9218, 1992.
Hirschmann et al., *J. Am. Chem. Soc. 114*: 9699–9701, 1992.
Eichler et al., *Biochemistry 32*: 11035–11041, 1993.
Patek et al., *Tetrahedron Letters 35(49)*: 9169–9172, 1994.
Hauske et al., *Tetrahedron Letters 34(31)*: 4909–4912, 1993.
Houghten et al., *BioTechniques 13(3)*: 412–421, 1992.
Gordon et al., *Journal of Medicinal Chemistry 37(10)*: 1385–1401, 1994.
Gallop et al., *Journal of Medicinal Chemistry 37(9)*: 1233–1251, 1994.
Lam et al., *Nature 354*: 82–84, 1991 (and attached correction Lam et al., *Nature 358*: 434, 1992).
Furka et al., *14th Int. Congs. Biochem. FR:013*, 1988.
Furka et al., *Int. J. Peptide Res. 37*: 487–493, 1991.
Houghten et al., *Nature 354*: 84–86, 1991.
Hebert et al., *Tetrahedron Letters 35(51)*: 9509–9512, 1994.
Hutchins et al., *Tetrahedron Letters 36(15)*: 2583–2586, 1995.
Terrett et al., *Bioorganic & Medicinal Chemistry Letters 5(9)*: 917–922, 1995.
Baldwin et al., *J. Am. Chem. Soc. 117*: 5588–5589, 1995.
Freier et al., *J. Med. Chem. 38*: 344–352, 1995.

*Primary Examiner*—Ponnathapura Achutamurthy
*Assistant Examiner*—P. Ponnaluri
*Attorney, Agent, or Firm*—Townsend and Townsend and Crew LLP

[57] ABSTRACT

Predetermined combinatorial libraries of non-peptide compounds are disclosed. Compounds useful for generating such libraries are also disclosed.

3 Claims, No Drawings

COMBINATORIAL NON-PEPTIDE LIBRARIES

TECHNICAL FIELD

The invention is directed to predetermined libraries of non-peptide compounds, and to related compounds useful for making such libraries.

BACKGROUND OF THE INVENTION

Random peptide libraries and protein diversity generated by means of phage display methodology are becoming invaluable for the identification of new small molecule drugs. These approaches that produce a large multiplicity of peptides are encompassed by the term "combinatorial chemistry." Early combinatorial chemistry efforts involved one or more variations on the Merrifield peptide synthesis scheme (R. Merrifield, *J. Am. Chem. Soc.* 85:2149–54, 1963). This scheme features incremental lengthening of a peptide chain on a solid phase support. Today, commercially available equipment can be used to perform peptide synthesis on solid supports. More specifically, after a first amino acid is attached to a solid support, a series of reactions involving deprotection, attachment of the next amino acid (protected) in the sequence, deprotection of the peptide, and so on, is carried out to generate a synthetic peptide or polypeptide. Peptide combinatorial libraries have been recently reviewed by M. Gallop et al., J. Med. Chem. 37: 1233–51, 1994 and E. Gordon et al., J. Med. Chem. 37: 1386–1401, 1994, for instance.

Large combinatorial libraries (containing millions and even billions of peptides) can now be generated and analyzed. By using standard, solid phase peptide synthesis methods in conjunction with a resin proportioning (split) and mix technique protocol (see, for instance, A. Furuka et al., Abstr. 14th International Congress of Biochemistry, Prague, Czechoslovakia, Vol. 5, p. 47, 1988; A. Furuka et al., *Intl. J. Pept. Protein Res.* 37:487–93, 1991; K. Lam et al., *Nature* 354: 82–84, 1991; and R. Houghten et al., *Nature* 354:84–86, 1991), equimolar mixtures of peptides with one unique sequence per bead can be produced. Deconvolution of these peptide libraries is accomplished by subjecting peptide mixtures (in solution) to bioassays in an iterative fashion (for instance, as described by R. Houghten et al., *BioTechniques* 13:412–21, 1992). By screening progressively smaller libraries and sub libraries of peptide mixtures, an active sequence(s) can be identified. Alternatively, solid phase-immobilized peptides can be screened using appropriately developed bioassays. Deconvoluted beads displaying a bioactive peptide sequence can then be sequenced using a peptide sequencer (see K. Lam et al., *Bioorg. Med. Chem. Lett.* 3:419–24, 1993).

There are advantages and disadvantages to each of these processes (i.e., using compounds in solution versus immobilized compounds for bioassay and deconvolution). Compounds in solution offer the following advantages: (1) compounds can be assayed in conjunction with soluble or insoluble receptors, enzymes or cell-based bioassays; (2) the molarity of compounds can be controlled; and (3) deconvolution strategies are readily available. The disadvantages of compounds in solution include: (1) complex mixtures in solution can result in multiple "hits"; (2) many compounds having low activity may be present in the same pool; (3) deconvolution can be elaborate and time-consuming; and (4) total pool concentrations cannot exceed a certain, limiting concentration.

Immobilized or insolubilized (for instance, on beads) compounds provide the following advantages: (1) ease of detection and selection of positive compounds; (2) no cleavage work-up is needed; (3) each bead or matrix unit is associated with a single compound that can be readily identified. The disadvantages of immobilized compounds include: (1) uncertain effects of the solid support on the activity of affixed compounds; (2) potential conformation constraints on the affixed compound and its activity; (3) the compounds are generally small, and naturally would interact with receptors or binding moieties in a small form, not as a small portion of a larger molecular entity; (4) the detection molecule (for instance, a receptor or enzyme in a bioassay format) must be soluble, and may need to be modified, configured or adapted to function appropriately in a solid phase assay format; and (5) membrane-bound detection molecules (such as receptors or in cell-based assays) may not be amenable to a solid phase assay format.

Methods have been developed for synthesis and deconvolution of nucleotide-encoded peptide libraries (N. Needels et al., *Proc. Natl. Acad. Sci. USA* 90:10700–04, 1993; R. Lerner et al., PCT Application WO 93/20242); chemically-tagged peptide libraries (A. Borchardt et al., *J. Am. Chem. Soc.* 116:373–74, 1994); and peptide-tagged non-sequencible libraries (V. Nikolaiev et al., *Pept. Res.* 6:161–70, 1993). Also, a multiple use library has been used to screen a G-coupled receptor system (C. Jayawickreme et al., *Proc. Natl. Acad. Sci. USA* 91:1614–18, 1994). Many of these libraries and assays have undergone limited testing and analysis. Thus, to make these libraries generally useful in conjunction with a spectrum of bioassays, especially cell-based and/or membrane-bound receptor assays, considerable improvements in these methods are needed.

To overcome limitations associated with reported peptide libraries, there is a need in the art for alternatives to known, peptide-based combinatorial libraries. The present invention provides such alternatives, as well as other, related advantages.

SUMMARY OF THE INVENTION

It is an object of the present invention to provide predetermined library of non-peptide compounds comprising a plurality of compounds of the formula:

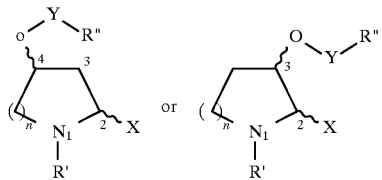

wherein X is COR, COR" or NHCOR"; Y is CO, $CH_2CO$, $CH_2SO_2$, $CH_2PO_2R$, $CH_2Ph-CO$, $CH_2Ph-SO_2$, or $CH_2Ph-PO_2R$; R is H or a substituted or unsubstituted alkyl, cycloalkyl, aryl, arylalkyl, heteroaryl, or heteroarylalkyl; and R' is COR, $SO_2R$, $PO_2R_2$, $CONR_2$, $CSNR_2$, or COOR; R" is OR, $NR_2$, $N(R)NR_2$ or $N(R)OR$; and n is 1 or 2.

Within one aspect of the invention, the stereochemistry at $C_2$ and $C_4$ is RR, RS, SR, or SS. Within another aspect of the invention, at least one of R, R' and R" has at least one chiral center.

These and other aspects of the invention will become evident upon reference to the following detailed description.

DETAILED DESCRIPTION OF THE INVENTION

Peptide libraries are a source of small molecules having enormous structural diversity and an even larger conformational diversity. Active peptides identified through bioassay screening ("lead peptides") can be quickly optimized by synthesizing a large number of analogs by combinatorial and/or parallel robotic synthesis. Peptide libraries generated using heterochiral amino acids, all D-amino acids and non-proteinogenic amino acids represent a rich source that can be mined for stabilized peptide leads. These peptide leads can be used to further identify peptidomimetic or non peptide lead compounds. Libraries made using heterochiral amino acids or cyclic peptides can also generate peptide leads which are enzymatically stable and have constrained conformation(s). These types of peptide leads also are readily developed into non-peptide or peptidomimetic lead compounds.

In the current era of drug development, high throughput screening of thousands to millions of compounds plays a key role. High throughput screening generally incorporates automation and robotics to enable testing these thousands to millions of compounds in one or more bioassays in a relatively short period of time. This high capacity screening technique requires enormous amounts of "raw materials" having immense molecular diversity to fill available capacity. Accordingly, combinatorial chemistry will play a significant role in meeting this demand for new molecules for screening. Once "leads" are identified using high throughput screening techniques, combinatorial chemistry will be advantageously used to optimize these initial leads (which analogs/variants will be tested in the same high throughput screening assay(s) that identified the initial lead). Thus, there is a need for new reagents and methods that can expand the scope of structural and conformational diversity contained within combinatorial libraries.

Generally in the past, years of effort were needed to develop peptidomimetics from peptide leads, This peptidomimetic development was typically achieved through laborious and cumbersome repetitive tasks involved in synthesizing a large number of analogs for structure-activity relationship (SAR) determinations. These manipulations included amino acid substitutions, peptide bond modifications, and introduction of conformational constraints. Such manipulations were followed by physicochemical characterization (such as nuclear magnetic resonance (NMR), circular dichroism (CD), and other spectroscopic methods) and computational chemistry, in order to develop models for synthesis of peptidomimetic leads. Today, a combinatorial approach used in conjunction with robotic technology can considerably reduce the time and effort needed for this exercise, and the chances of a successful outcome are vastly improved. Furthermore, as computational and spectroscopic methods for conformational analysis continue to improve, the time lag between identification of a peptide lead and testing of a stabilized peptide or peptidomimetic drug will be further reduced.

In general, combinatorial chemistry involves linking together, in step-wise fashion, identical or non-identical building blocks ("monomeric units", "chemical groups", "resin components" and the like). The potential number of combinations and permutations that can be generated through this technology are essentially infinite. For instance, if 10 distinct components can serve as building block 1, and 10 distinct components can serve as building block 2, so as to create a library of compounds described as "building block 1—building block 2", then 100 (10×10) unique compounds can be generated. If 10 distinct components can serve as building block 3, so as to create a library of compounds described as "building block 1—[covalently coupled to]—building block 2—[covalently coupled to]—building block 3", then 1,000 (10×10×10) unique compounds can be generated. As the number of variable within each building block increase, and/or as the number of building blocks increase, the size of the resultant library expands dramatically. Building blocks and monomers can be chemically conjugated to create a libraries containing components that are 100 to 1000 to 10,000 to 100,000 to 1,000,000 (and so on) building blocks in length. Reordering the building blocks singly, in tandem, in threes, and the like, can also generate diversity. Likewise, one or more repeats of the same building block can generate even more diversity.

One of skill in the art will recognize that, in some instances, building blocks or monomers may be assembled "backwards", particularly if the resultant library is designed to be analogous to a peptide library. That is, the last building block added to the "growing chain" may be analogous to the 5' terminal end ("front end") of a peptide or polypeptide. Thus, in a library schematically depicted as "A'—BFU'—AA'". the "A" building block or monomeric unit may be chemically conjugated to adjoining unit BFU last in time. However, the chemical characteristics of the A' subunit mimic the characteristics of a 5' peptide terminus, rather than a 3' peptide terminus. In this scheme, monomeric unit "AA: is generally attached to a solid phase matrix, until release of A'—BFU'—AA' following the last chemical conjugation reaction. As used herein, the presence of "'" after terms such as "building block 1'", "monomer 1'", "M1'" and "AA'" indicates that the monomer unit, building block or the like has been chemically conjugated (i.e., covalently linked or coupled) to an adjoining monomer unit or building block. After chemical conjugation, the monomer unit or building block is altered; for instance, upon reaction to form a covalent bond, the monomer can lose a water or ammonia molecule, or can undergo formation of a urea or carbamate group. Since there are innumerable variations in the nature of building blocks or monomers, and in the types of chemical reactions by which they can be chemically conjugated, for clarity and generality, reference is made to pre-reacted monomers ("M1") and to altered monomers post-reaction ("M1'")

The present invention discloses a variety of approaches that can be used to generate alternative combinatorial peptidic and non-peptidic libraries. These alternatives are described below.

A. PSEUDOPEPTIDE (PEPTIDERGIC) OLIGOMERIC LIBRARIES

A principal disadvantage associated with peptidic drugs is the low metabolic stability of these drugs due to in vivo proteolysis. One technique for overcoming this problem is replacement of some or all peptides with more proteolytically-stable building blocks or monomeric units, such as carbamates. Oligocarbamate libraries have been proposed, prepared and tested (C. Cho et al., *Science* 261: 1303–05, 1993). Another approach features preparation of oligomers of N-substituted glycines (R. Simon et al., *Proc. Natl. Acad. Sci. USA* 89: 9367–71, 1992; Bartlett et al., PCT Patent Application WO 91/19735, 1991). The "1:4 relationship of side chains" in peptides denotes that a side chain of amino acid "n" is separated from a side chain of adjacent amino acid "n+1" by 4 atoms. This 1:4 relationship of side chains present in peptides is maintained in N-substituted glycine oligomers, but the side chains are attached to nitrogen (N) atoms, rather than to carbon (C) atoms. Libraries of these oligomers, designated as "peptoids", are achiral and have been made and tested. Oligocarbamates, however, have a 1:6 side chain relationship.

Other peptide bond surrogates that have been used to replace one or more scissile bonds in bioactive peptides have 1:4, 1:5 or 1:6 side chain relationships. These modifications can lead to significant changes in conformation and/or spatial orientation of side chains, making predictions of structure (and conformation)-function relationships difficult. However, these potential complications can be generally ignored, if such enzymatically stable building blocks (e.g., peptide bond surrogates) are used in a combinatorial chemistry approach to generate and screen a library having huge molecular and conformational diversity. More specifically, since peptide bonds are replaced by modified peptide bonds or surrogate peptide bonds that are not cleaved by enzymes, resistance to in vivo proteolysis is enhanced.

A variety of peptide bond modifications, surrogates and isosteric replacements have been introduced to prepare bioactive peptide analogs with more favorable pharmacokinetics (A. Spatola, *Chem. Biochem. Amino Acids and Proteins* 7:267–357, 1983). Peptide analogs containing thioamide, vinylogous amide, hydrazino, methyleneoxy, thiomethylene, phosphonamides, oxyamide, hydroxyethylene, reduced amide and substituted reduced amide isosteres and β-sulfonamide(s) have been developed, as shown below.

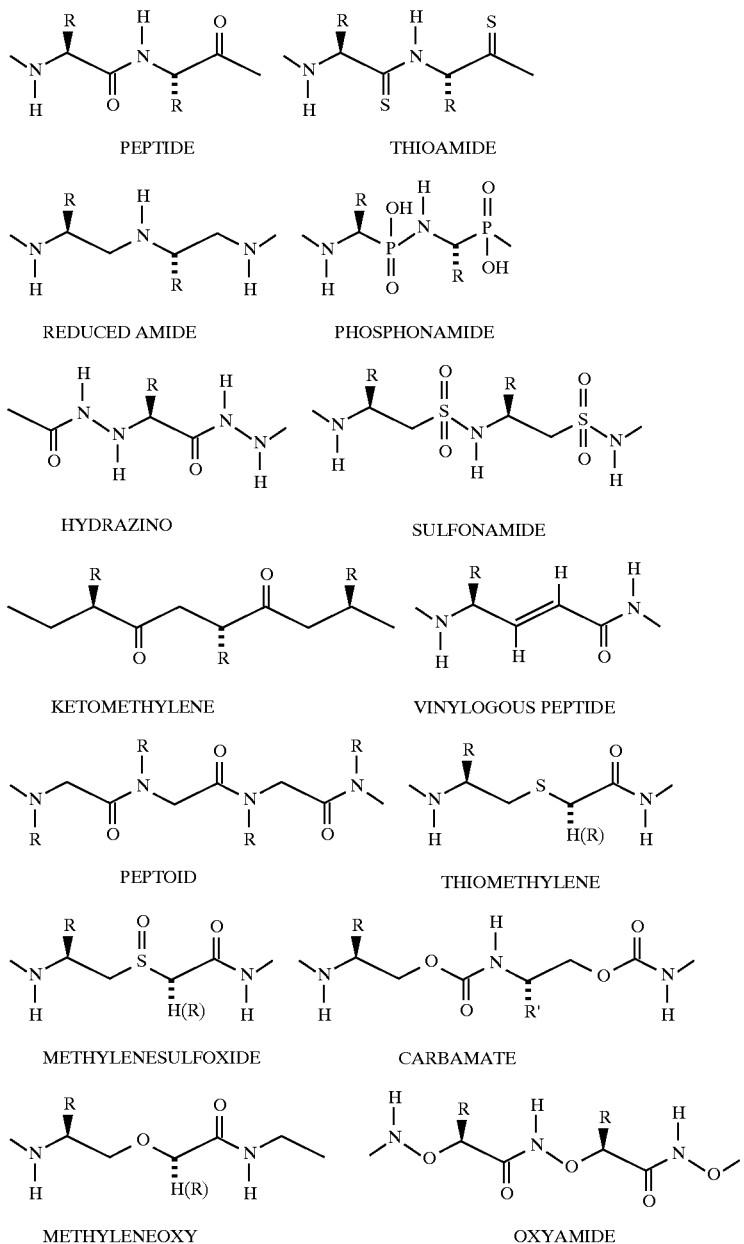

Stabilized oligomers containing such peptide analogs (in a peptide or peptoid format) permit generation of the molecular diversity inherent in peptide libraries. However, in contrast to peptide libraries, at the time of identification of lead compounds through bioassay screening, peptide analogs already possess linkages stable to proteolysis and/or acidolysis. Therefore, a collection or library of lead peptide analogs does not have to be designed, synthesized and tested after identification of a bioactive lead peptide, saving time and resources.

In one aspect of the present invention, modified amino acids, α-aminomethyleneoxy acetic acids (an amino acid-Gly dipeptide isostere), and α-aminooxy acids are synthesized from amino alcohols or α-bromo acids, according to the schemes depicted below.

Scheme II

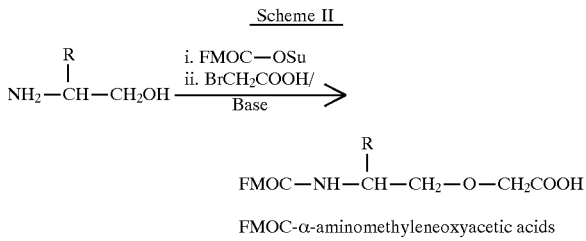

FMOC-α-aminomethyleneoxyacetic acids

Scheme III

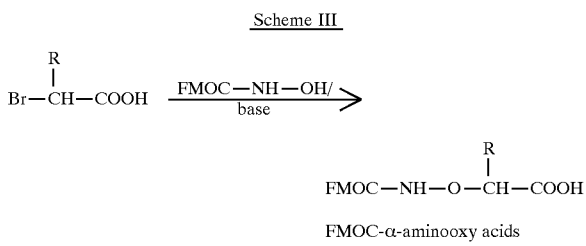

FMOC-α-aminooxy acids

These building blocks are used to generate pseudopeptide libraries by synthetic peptide combinatorial library (SPCL) methodology. These pseudopeptides of the present invention exhibit more flexibility than regular peptides, and therefore traverse a much wider conformational space than corresponding peptides. The pseudopeptides described herein are also more resistant to proteolysis than their peptide counterparts, and thus have an improved pharmacokinetic profile.

In another aspect of the invention, a pseudopeptide library of N-substituted aminocrotonic acids is generated directly on Wang resin, as shown in the scheme depicted below.

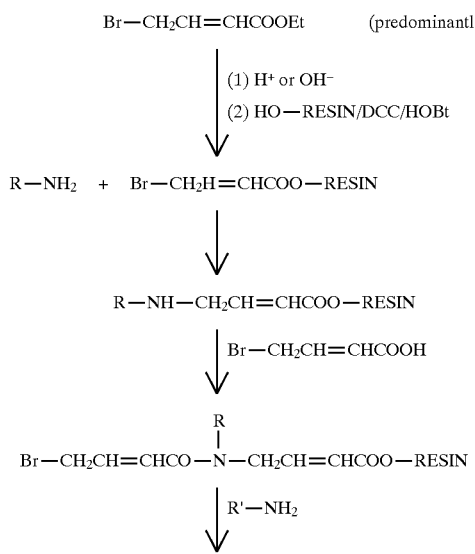

-continued

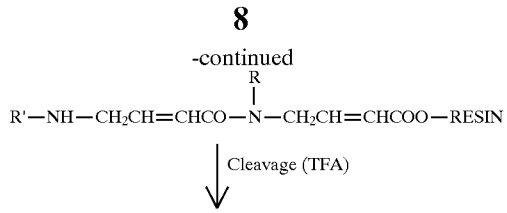

Cleavage (TFA)

R'—NH—CH₂CH=CHCO—N—CH₂CH=CHCOOH
                         |
                         R

This library will contain pseudopeptides that are achiral and proteolytically stable (due to the presence of N-alkylated amide bonds and rigid E-configuration of olefinic bonds). Furthermore, due to the presence of olefinic bonds, the pseudopeptides of this embodiment have much less flexibility, as compared to their peptide counterparts.

B. PEPTIDOMIMETIC LIBRARIES AND SCAFFOLD APPROACH

Using a conventional peptide-derived drug design scheme, a peptide lead is analyzed to determine which bioactive conformation presents certain side chains in a certain spatial orientation. The resultant model can then be translated into a non-peptidic moiety that possesses the same peptide side chain elements with a similar topological orientation. For instance, mimetics of certain conformational motifs, such as β-turns, may be used to advantage in this modeling/design protocol.

Peptide mimicry relies on biorecognition and message transduction mediated by the interaction of one or more peptide ligands with their corresponding target receptors. This ligand-receptor interaction is believed to depend on the presentation of certain side chain elements of amino acids in a particular topological arrangement. Peptide mimicry presumes (i) that the backbone of a peptide essentially acts as a scaffold that presents side chain elements in a defined architecture; and (ii) that amino acid sequence determines the presence or absence of a required conformation in an energetically accessible equilibrium. Screening of a library wherein molecular diversity is generated by putting amino acid side chains on rigid scaffolds of diverse topological and stereochemical orientations should lead to peptidomimetics in a structural as well as a functional (agonistic or antagonistic) sense.

For instance, a hexapyranose sugar (e.g., glucose) is an exemplary scaffold, wherein 4 —OH groups of the sugar can be used in combinatorial fashion with side chains of only 20 naturally occurring amino acids. The resultant library would contain 160,000 potential peptidomimetics. Recognizing that 16 (eight pairs of enantiomers) stereo isomers of this hexopyranose sugar are available, this set of "stereo isomer libraries" would yield 2,560,000 tetrapeptide mimetics. Such stereochemical diversity would reflect not only the sequential diversity of a linear tetrapeptide, but would also represent a significant portion of the conformational space and diversity available from a tetrapeptide. While optimizing this particular type of scaffold/amino acid side chain system may require development of appropriate chemistries applicable to the entire collection of sugar scaffolds, this approach can be readily used with a limited number of sugars, or with other easily accessible or commercially available scaffolds. Some commercially available scaffolds are depicted below.

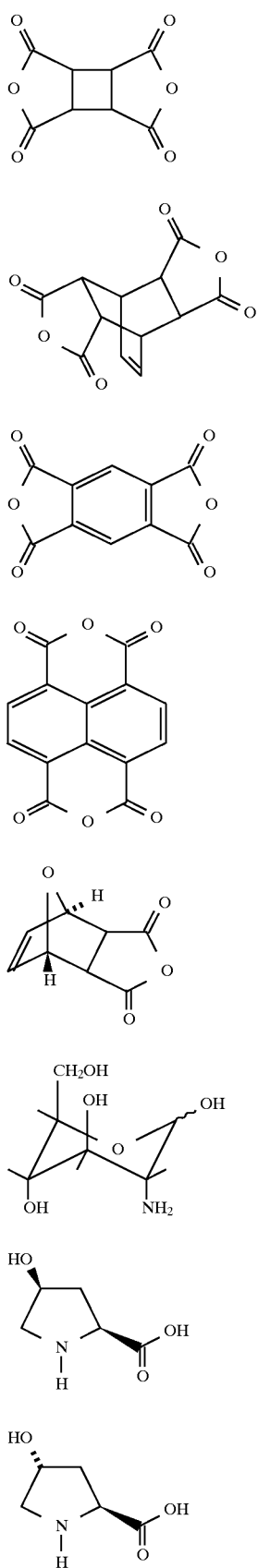

(1)

(2)

(3)

(4)

(5)

(6)

(7)

(8)

-continued

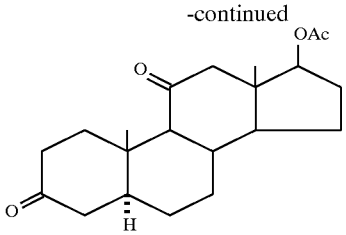
(9)

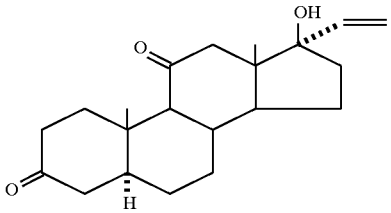
(10)

Amino acid side chains can be classified as aliphatic, lipophilic, aromatic, polar H-bond acceptors and donors, and positively- and negatively-charged. By placing such amino acid side chains on a variety of rigid and stereochemically defined scaffolds, a significant diversity of peptidomimetic leads should be generated. This diversity can be increased several-fold by additionally employing as side chains a large number of amines and carboxylic acids that are commercially available.

Other "biorecognition elements" may also be advantageously used to create diverse peptidomimetic libraries using the scaffold approach. For instance, nature uses two other building blocks, e.g., carbohydrates and nucleotides, as oligomeric molecular recognition elements. Libraries of carbohydrates may be an important source of molecular diversity, since, in principle, oligosaccharides are capable of generating much greater diversity than peptides and nucleotides. Oligonucleotides also represent a feasible approach to creating diverse libraries of compounds. In addition to translating such oligonucleotides to peptides, such libraries also can be used to develop antisense leads or to identify oligonucleotides that interact agonistically or antagonistically with proteins. With oligonucleotides, sugar-phosphate bonds serve as a "scaffold" on which purine and pyrimidine bases are arranged in a sequence and in a topologically defined fashion. Non-nucleotide oligomers that can present purine and pyrimidine bases on an alternative backbone, such as peptide-nucleic acids (PNAS) or other appropriate scaffolds, therefore represent another approach to peptidomimetic drug design through combinatorial chemistry. Moreover, drug design that is based on interactions with specific genomic elements will become a more fertile area for study as sequencing of the human genome proceeds and numerous therapeutic targets (both genomic and gene products) become available.

In a one aspect, scaffolds that are commercially available or are easily synthesized and appropriately functionalized for attaching amino acid side chains or other biorecognition elements are selected. Exemplary scaffolds in this regard include bisanhydrides, anhydrides, glucosamines, hydroxyprolines, and steroids. In a preferred embodiment, the selected scaffold is a bisanhydride of cyclobutane tetracarboxylic acid or benzene 1,2,4,5- tetracarboxylic acid. A synthetic scheme for a bisanhydride scaffold-based library is summarized as follows. A bisanhydride scaffold was linked to Wang resin, releasing a carboxylic acid group. This carboxylic acid group was successfully protected as an allyl ester. The second anhydride was successfully opened with amines subsequent to the opening of the first anhydride.

After coupling the resultant free carboxylic acid group to an amine, the allyl ester was deprotected, and the resulting free carboxylic acid again coupled to an amine. Finally, cleavage of the resin with BBr₃ and an amine provided the tetraamide product. A mixture of two racemates should result from use of pure cis-cis exo and endo isomers; a mixture of four racemates should result from use of a mixture of exo and endo bis anhydrides. These isomers can be separated by HPLC and characterized by 2D NMR.

Additional exemplary scaffolds and/or scaffold libraries are depicted schematically below.

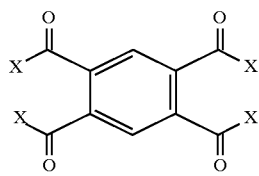

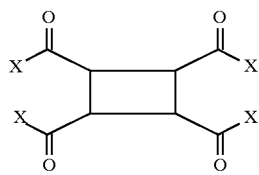

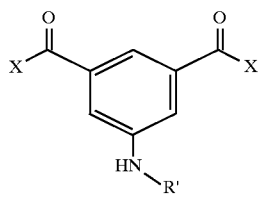

Where,

X=—OR, —NR₂, —N(R)NR₂, —N(R)OR

R'=—COR, —SO₂R, —PO₂R₂, —CONR₂, —CSNR₂, —COOR

R=H, alkyl, cycloalkyl, aryl, arylalkyl, heteroaryl, heteroarylalkyl and and any of their substituted analogues.

Planar Tetra-Functionalized Scaffolds

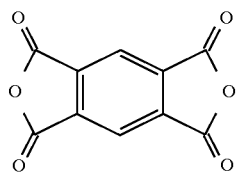

Benzenetetracarboxylic dianhydride

Planar Tetra-Functionalized Scaffolds

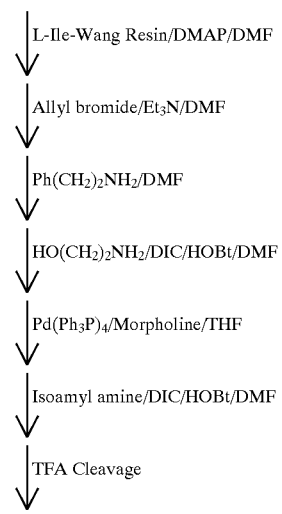

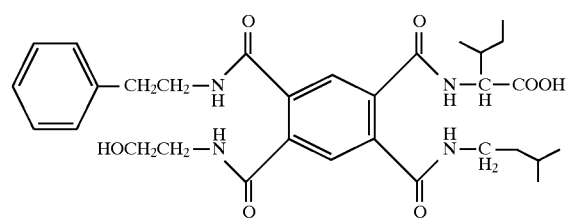

Cyclic tetrapeptide-mimetic with benzene ring as scaffold

Planar Tri-Functionalized Scaffolds

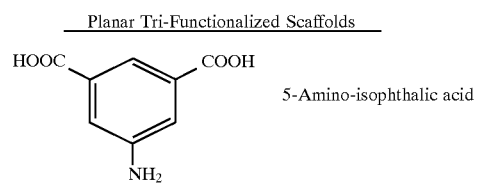

5-Amino-isophthalic acid

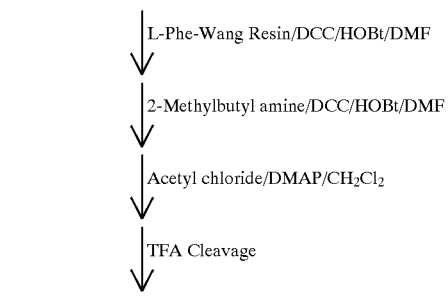

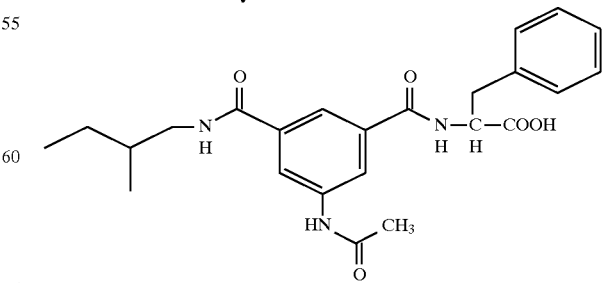

Cyclic tripeptide-mimetic with benzene ring as scaffold

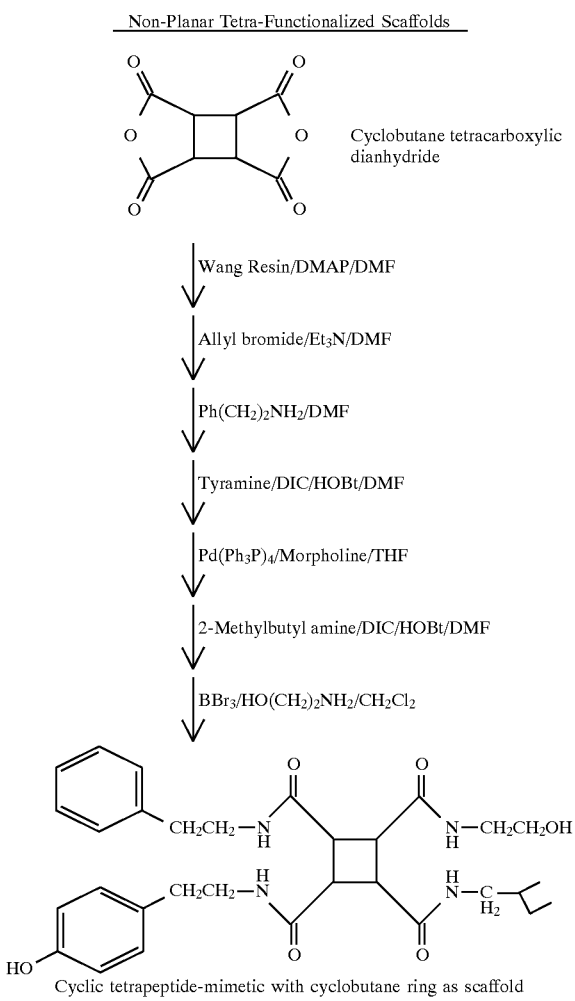

Cyclic tetrapeptide-mimetic with cyclobutane ring as scaffold

C. NON-PEPTIDIC SMALL MOLECULE "LIBRARIES" AND "COMBINATORIAL LIBRARIES"

Non-oligomeric molecular libraries generated by parallel, multiple syntheses can be obtained using conventional solution chemistry and liquid handling robotics. This approach has limited general utility, however, since it features predominantly single step synthesis, and the resultant type and number of compounds is relatively small. A combination of "split and mix" and "tea bag" protocols has been described by R. Houghten, Proc. Natl. Acad. Sci. USA 82:5131–35, 1985. Organic synthesis on a solid phase matrix by parallel, multiple syntheses (e.g., synthesis of benzodiazapines and hydantoins (S. Hobbs DeWitt et al., Proc. Natl. Acad. Sci. USA 90:6909–13, 1993); of benzodiazapines, prostaglandins and β-turn mimetics (B. Bunin et al., J. Am. Chem. Soc. 114:10997–98, 1992) may be used to achieve rapid synthesis of analogs. Alternatively, small molecule diversity may be generated using the multicomponent Ugi reaction (R. Armstrong, CHI conference on Exploiting Molecular Diversity, Jan. 12–14, 1994, San Diego, Calif. USA). Organic synthesis using solid supports and polymer-supported reagents has been previously reported (C. Leznoff, Acc. Chem. Res. 11:327, 1978). Over the last two decades, many types of reactions and reagents have been developed, notable more for their novelty than for their general utility. However, with the current interest in combinatorial chemistry, this area has drawn new attention. Developments relating to the chemistry of solid phase peptide synthesis, including the development of specialty resins, linkers, orthogonal protection schemes, automation and robotics, now enable one to perform solid phase organic synthesis of small molecules in a practical parallel or combinatorial fashion. Therefore, there exists a vast opportunity to employ innovative uses of principles and technologies of organic synthesis, peptide synthesis, and peptide combinatorial synthesis to generate petidergic, peptidomimetic and small molecule libraries comparable in size and complexity to peptide libraries.

In one aspect of the invention, an ISIS data base search of ACD (Available Chemical Directory) was used to identify potential building blocks. Many monofunctional, bifunctional, ambident bifunctional (e.g., anhydrides), and multifunctional building blocks were identified. These building blocks have advantageous reactive functionalities, such as hydroxyl, amino, carboxyl, isocyanate, isothiocyanate, halide, acyl halide and anhydride groups. More than 250 isocyanates, 400 thiocyanates, 3000 sulfonic acids and 130 anhydrides, in addition to proteinogenic and non-proteinogenic amino acids, were thereby identified. These commercial building blocks represent a huge structural diversity that can be employed in combinatorial methods to generate a rich source of molecular diversity.

In another aspect of the invention, bifunctional building blocks, such as natural and unnatural amino acids, are linked to a solid support (e.g., Wang resin). After reacting the amino group of the amino acid with a reactive monofunctional building block, the compound can be cleaved from the resin with $BBr_3$ in the presence of an amino monofunctional building block. More specifically, an amino acid linked to the Wang resin can be coupled with a variety of aliphatic, aromatic and heteroaromatic carboxylic acids, followed by cleavage with $BBr_3$ and commercially available amines to provide a structurally diverse library. From a bank of 100 building blocks in each set (amino acids and monofunctional building blocks), a library of one million novel compounds can be generated using a multiple peptide synthesizer.

In another aspect, amino acids linked to the solid phase resin can be reacted with a diverse set of ambident bifunctional compounds (such as anhydrides), releasing a carboxylic acid group. The free carboxylic acid group can then be coupled with a diverse set of amines, followed by cleavage with trifluoroacetic acid (TFA) to yield a library of novel and structurally diverse compounds. Again, by combining 100 molecules of each of the building blocks, a library of 1 million compounds will result. This non-peptide building block strategy is attractive because anhydrides, an exemplary group of ambident bifunctional compounds, represent a wide range of cyclic structures (scaffolds) having significant stereochemical diversity. By presenting a very large structural diversity within the initial pools that are tested in the first round of screening, interference in the bioassays by closely related compounds is minimized. During subsequent screening rounds, active leads can be optimized by making libraries from closely related building blocks.

D. OTHER LIBRARIES

1. Pharmacophores

Certain pharmacophores, such as benzodiazepines and hydantoins, have frequently been associated with many selective biological activities. A variety of benzodiazepines have shown selective therapeutic actions, and therefore application as anxiolytics, sedatives, CCK antagonists, PAF antagonists, HIV reverse transcriptase inhibitors, and opioid antagonists. Development of a solid phase synthesis protocol (multicomponent and combinatorial) to identify analogs of any well-established, orally available, and well-tolerated pharmaceutical is an attractive strategy for drug discovery. Homologs and analogs of benzodiazepines may be synthesized in combinatorial fashion from β-aminosulfonic acids and/or α and β-amino phosphonic acids. A new solid phase synthesis scheme for such analogs can be based on amino acid-like trifunctional building blocks.

Solid phase synthesis of substituted and functionalized heterocycles, such as imidazoles, indoles, quinolines, isoquinolines and the like, can also be adapted to combinatorial methods. The MDDR (MACCS Drug Data Report) data base can be accessed to identify frequently observed pharmacophores having high combinatorial potential.

Synthesis of a benzo[3,4a]-1,2,6-thiadiazocin-1,1-dioxide ("benzodiazepine-like") compound is depicted below.

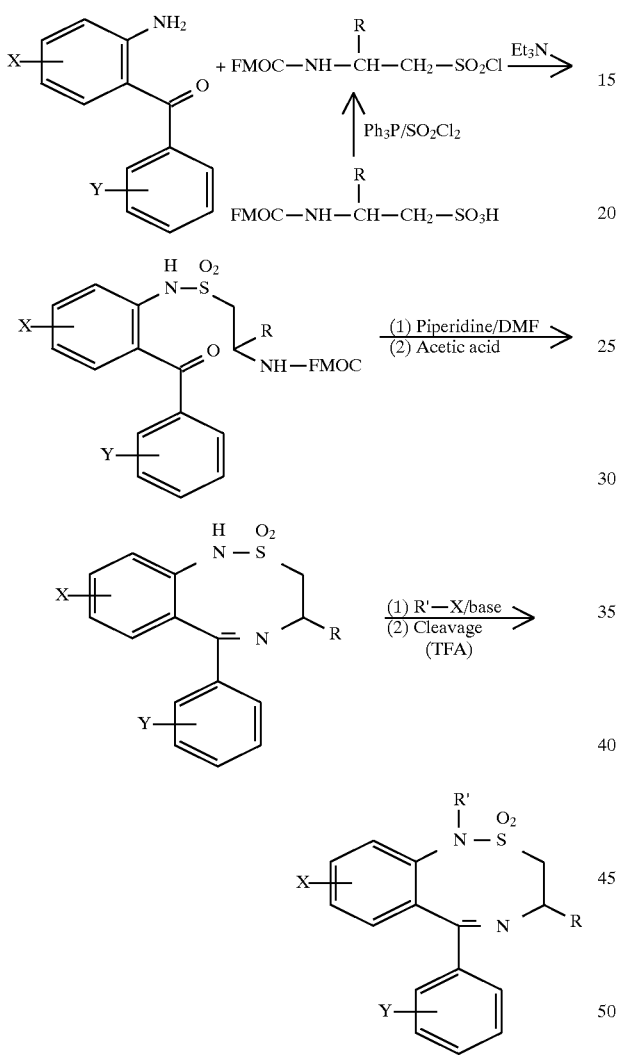

Synthesis of a more generalized "benzodiazepine-like" compound is depicted below.

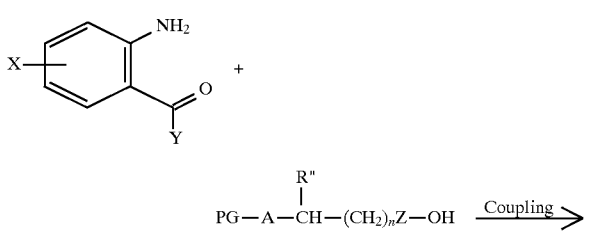

Linkage to resin through functional groups in either X or Y or R"

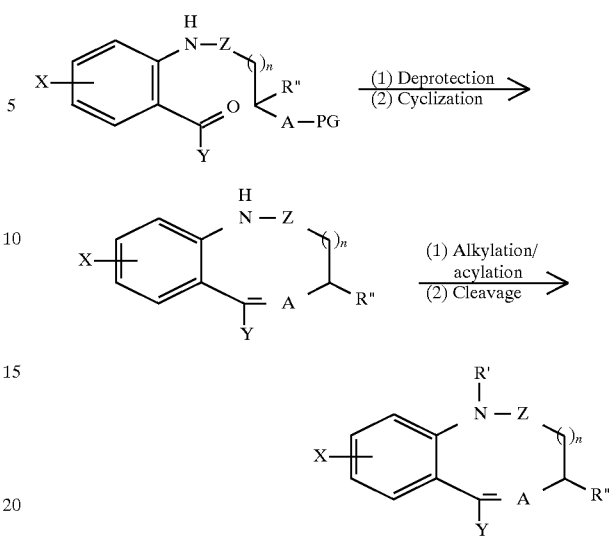

A more generalized, exemplary "benzodiazepine-like" library may be represented as follows:

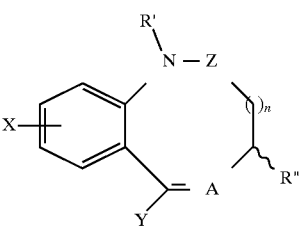

wherein

X is OR, F, Cl, Br, $CF_3$, $NO_2$ or R";

Y is H or a substituted or unsubstituted alkyl, alkenyl, alkynyl, cycloalkyl, aryl, arylalkyl, heteroaryl, or heteroarylalkyl;

A is N, N—O, N—NH, or N—$CH_2$;

Z is CO, $SO_2$ or $PO_2R$;

R' and R" are selected from the group consisting of R, COR, COOR, $(CH_2)_n$COOR, $(CH_2)$CONR$_2$, NRCOR, NRCOOR, $(CH_2)_n$CON(R)NR$_2$, $(CH_2)_n$CON(R)OR, $(CH_2)_n$NRCOR, $(CH_2)_n$NRSO$_2$R, $(CH_2)_n$NRPO$_2$R$_2$, $(CH_2)_n$NR$_2$, $(CH_2)_n$NRCONR$_2$, $(CH_2)_n$NRCSNR$_2$, $(CH_2)_n$OR, $(CH_2)_n$OCOR, $(CH_2)_n$OCONR$_2$, $(CH_2)_n$PhOR, $(CH_2)_n$PhOCOR, $(CH_2)_n$PhOCONR$_2$, $(CH_2)_n$SO$_2$NR$_2$, and $(CH_2)_n$PO$_{2R}$NR$_2$; and n is 0 or 1.

2. Organic Reactions on Solid Supports

Multicomponent reactions, such as the Ugi reaction for the synthesis of amino acids or the Mannich reaction, if adapted to a solid phase format, can be amenable to generation of molecular diversity. For instance, the three component Mannich reaction can generate an aXbXc (where "a, b and c" represent the number of compounds available for each component; e.g., aldehyde, secondary amine and active methylene compound, as an example) number of compounds in combinatorial fashion, so long as any one of the Mannich components can be reversibly tethered to a solid support. Amino acids linked to resin, as depicted below, can be a suitable, tetherable component.

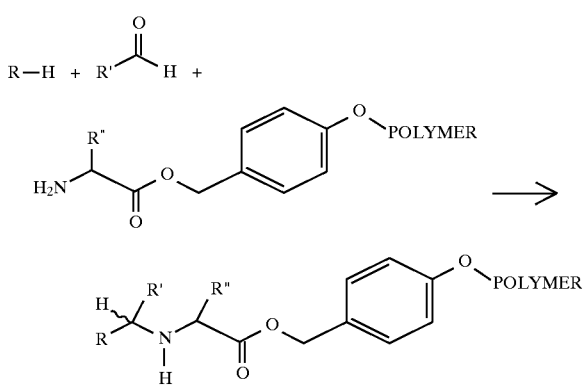

Other chemical reactions, including Diels-Alder reactions, cycloaddition reactions, a Wittig reaction, alkylation, and organometalic reactions, can be harnessed in a solid phase format to generate scaffold and molecular diversity. In general, exploring and expanding the scope of key and/or fundamental organic reactions on solid supports can generate diversity of new and novel combinatorial molecules.

3. Targeted Drug Discovery and Optimization

If some information is available regarding a potential target (e.g., enzymes or receptors), or in the event that initial or putative leads are available, combinatorial chemistry can generate a spectrum of chemical diversity most likely to yield leads and/or to assist in rapid lead optimization. Synthesis of enzyme inhibitors is particularly amenable to this approach. By substituting stataine (for aspartyl proteases); amino aldehydes, fluoroketones and ketomethylene peptide bond surrogates (for serine, cystine and aspartyl protease); and phosphonate or aminophosphonic acids (for metalloproteases) in place of the scissile peptide bonds of peptide substrates, then oligomerizing the building blocks with other building blocks (including amino acids), libraries of potential enzyme inhibitors with appropriate selectivity can be generated.

4. Screening Improvements

Screening technologies are undergoing, and will continue to undergo, considerable changes and improvements, especially with regard to functional screening techniques. One aim is development of simple and rapid functional assays that can identify one or more active ingredients in tested pools without the need for a long deconvolution process. Substantial improvements in chemistry and assay techniques will be key to achieving generalized, routine use of such assays. For instance, the scope and versatility of organic reactions conducted on solid supports are increasing. Such improvements will enrich methods and diversity relating to small molecule combinatorial libraries.

Robotics used in conjunction with high throughput screening methods have only recently experienced general use. Development of robotics systems that can handle large numbers of resin samples for proportioning, mixing, cleavage and sample-handling will continue to be developed. Moreover, robotics that can perform multiple chemical reactions at variable temperatures, and subsequently handle work up and spectroscopic characterization of bioactive leads, are or will become generally available. Manipulation of libraries containing billions of compounds will provide an impetus to improve resin loading and handling capabilities. With the availability of new assay formats, partially cleavable libraries can be advantageously employed, and solid phase assays to identify enzyme inhibitors and ligands for soluble receptors will become available. Additional selection means that enable identification of active compounds within enormous combinatorial libraries can feature affinity enrichment or affinity selection, followed by mass spectroscopic identification of any bioactive compound.

E. PROTOTYPICAL BUILDING BLOCK APPROACH

An exemplary procedure for generating a combinatorial library using the building block approach is disclosed. Definition of the following terms and abbreviations may be helpful to an understanding of this section:

Wang resin: p-benzyloxybenzyl alcohol copolystyrene-divinyl benzene (DVB) resin

Chlorotrityl resin: 2-chlorotritylchloride copolystyrene-DVB resin

Merrifield resin: chloromethylated copolystyrene-DVB resin

PAM resin: 4-hydroxymethyl-phenylacetamidomethyl resin

Knorr resin: 2,4-Di—$CH_3O$—Ph—CH(NH-Fmoc)—Ph—4'—$OCH_2$—CONH—$CH_2$—Ph polymer resin Rink amide resin: 4-(2'4'-dimethoxyphenyl-Fmoc-aminomethyl)-phenoxy copolystyrene-DVB resin MAP: multiple antigen peptide MBHA resin: p-methylbenzhydrylamine resin TENTA gel: composite of polyethylene oxide grafted onto a low cross-linked polystyrene gel-type matrix HMPB: 4-hydroxymethyl-3-methoxyphenoxybutyric acid co lolystyrene-DVB resin HOAt: 1-hydroxy-7-azabenzotriazole DIC: 1,3-diisopropylcarbodiimide HATU: [O-(7-azabenzotriazol-1-yl)-1,1,3,3-tritetramethyluronium hexaflurorophophate]

HOBt: N-hydroxybenzotriazole

HBTU: 2-(1H-benzotriazol-1-yl)-1,1,3,3-tetramethyluronium hexafluorophosphate

Fmoc: 9-fluorenylmethyloxycarbonyl

DMF: N,N-dimethylformamide

NMP: N-methylpyrrolidinone

TFA: trifluoroacetic acid

NMR: nuclear magnetic resonance

Briefly, resins were weighed so that each represented the same nmole scale (based on loading). Exemplary resins in this regard include standard Wang resins with a naturally occurring amino acid preloaded, as well as other resin types, such as chlorotrityl, Merrifield, PAM, Rink Amide, MAP, MBHA, TENTA gel, Knorr, and HMPB. One of ordinary skill in the art will recognize that any other resin that can be loaded with a bifunctional unit may be suitable for use in this regard. The term "bifunctional unit" means any compound having two different functionalities that can be selectively protected/de-protected, or any ambident compound, such as an anhydride.

Wang resins containing naturally occurring amino acids were then combined in a separate step. Briefly, the resins were stirred on a magnetic stirrer for >2 h to form a homogeneous mixture. The homogeneous resin mixture was then split into equal portions. The number of portions was dependent on the number of bifunctional groups to be reacted with the resin mixture. Using standard peptide chemistry, the resins were de-protected with 25% piperidine.

Coupling chemistries suitable for use within the present invention are not limited to peptide chemistries, but can include any chemistry that serves to couple bifunctional units to the groups attached to the resin. Exemplary chemistries in this regard include, but are not limited to, the formation of carbamates, ureas and esters. Bifunctional units were coupled to the de-protected resins using HOAt/DIC chemistry. One of ordinary skill in the art will recognize that other chemistries that are consistent with the functionality of the coupling agents, such as HOAt/HATU, HOBt/DIC, HOBt/HBTU and the like, may be suitable for use in this regard. Each bifunctional unit was triple coupled. In a preferred embodiment, all bifunctional units were Fmoc-protected.

After complete coupling (followed by ninhydrin testing), the resin samples were combined into one large batch and stirred for >2 h on a magnetic stirrer. Other calorimetric detection systems or high-resolution $^1$H NMR on the solid support using a NANO-PROBE® (Varian Associates, Palo Alto, Calif.) may also be used to determine coupling completeness. The resin mixture was then split into an appropriate number of pools for the next coupling reaction. In each pool, the bifunctional units were de-protected using 25% piperidine. The free amines were then coupled to the bifunctional units using standard peptide chemistry appropriate to a variety of acidic compounds. At each step during the synthesis of this prototypical combinatorial library, the compounds are thoroughly washed with DMF to remove any unreacted reagents and by-products.

In this prototypical example, each pool is coupled with a specific acid compound. Therefore, the identity of the final coupled group is known for each pool. This final step is equivalent to capping in standard peptide synthesis.

The final step of the synthesis involves cleavage of the compounds from the resin into vials. The compounds are then lyophilized to remove the TFA and other volatiles from the mixtures. This step is repeated several times to ensure complete removal of all volatile components. The pools are then screened as mixtures (similar to natural product screening) for bioactivity in various assays. After screening, any interesting or active compound pools are re-synthesized as sub-libraries, wherein the combine and split steps are incrementally removed in a reverse direction. Alternatively, a recursive de-convolution may be applied.

F. PROTOTYPICAL PSEUDOPEPTIDE APPROACH

An exemplary procedure for generating a combinatorial library using the pseudopeptide approach is described.

In step (1), a series of FMOC-protected α-aminooxy acids and α-amino acids are collected, either from commercial sources or synthesized according to the standard procedures. For example, combining 8 L- or D-α-aminooxy acids and 12 L- or D-α-amino acids together makes four groups of 20 monomers each. These monomers can be oligomerized to obtain libraries of pseudopeptide trimers, tetramers or higher order oligomers of any desirable length.

In step (2), combinatorial library synthesis using these monomers is carried out in several steps. First these monomers are loaded in equimolar amounts onto Rink Amide resin or any other suitable resin known in the art of organic synthesis and peptide synthesis. The loading of each monomer is carried out in a reaction vessel (RV) using a suitable excess of the monomer and any coupling reagents and additives known in the prior art of organic synthesis and peptide synthesis. The reaction is allowed to take place for a fixed amount of time. The entire coupling protocol is repeated again (or is repeated multiple times), until all the resin has undergone complete conversion to the products. Completeness of the reaction can be followed using methods known in the art of organic synthesis and peptide synthesis, including but not limited to calorimetric tests (such as a ninhydrin test), analytical methods (such as high performance liquid chromatography (HPLC)), and spectroscopic methods (such as proton nuclear magnetic resonance ($^1$H NMR)).

In step (3), the loaded resins are combined together and then split into an equal number of portions (A. Furka et al., 14th Intl. Congr.Biochem. 5:47, 1988), depending upon the number of monomers to be used in the subsequent step.

In step (4), the resin mixture in each RV is deprotected with piperidine in DMF.

In step (5), to the resin in each RV is added an excess of a monomer, a coupling reagent, and an additive (such as those known to one of ordinary skill in the art of organic synthesis and peptide synthesis). The reaction is allowed to take place for a fixed amount of time, and the coupling protocol is repeated again (or several times) until all the resin has undergone complete conversion to the products (as determined by methods described above in step (2)).

In step (6), steps (3), (4) and (5) (in that order) are then repeated the appropriate number of times so that the penultimate monomer has been coupled.

In step (7), step (3) is then repeated once more, except that the resin is split into twice the number of pools as before.

In step (8), step (4) is then repeated for all the pools.

In step (9), step (5) is then done in duplicate for each monomer to be coupled in the last position.

In step (10), step (4) is then repeated for all the pools.

In step (11), the resin in one half of the duplicate sets is capped with a carboxylic acid, a sulfonic acid, an isocyanate, an isothiocyanate, or a chloroformate; the resin in the other half of the duplicate set is left unreacted.

In step (12), the resin in one-half of the duplicate sets is capped at its N-terminus with a carboxylic acid, a sulfonic acid, an isocyanate, an isothiocyanate, a phosphonic acid, or a carbamyl chloride to form an amide, a sulfonamide, a urea, a thiourea, a phosphonamide, or a carbamate, respectively, while the resin in the other half of the duplicate set is left free.

In step (13), the cleaved products are collected by evaporation of all volatile components in vacuo and lyophilization and/or ether precipitation.

In step (14), the products from each pool are dissolved in a sufficient amount of dimethylsulfoxide (DMSO) and, after appropriate dilutions, screened for various bioactivities.

In step (15), if any pool is found to be active in any of the screens, the pool is reiteratively deconvoluted by synthesis and screening of sub-libraries (see, e.g., R. Houghten et al., Nature 354:84, 1991).

G. PROTOTYPICAL SCAFFOLD APPROACH

An exemplary procedure for generating a combinatorial library using the scaffold approach is described.

In step (1), a novel and/or unique orthogonally-protected tri-functional scaffold is designed and synthesized by methods known in the prior art of organic synthesis. For example, compound 1, below, is synthesized in four steps from commercially available Boc-trans-4-hydroxy-L-proline.

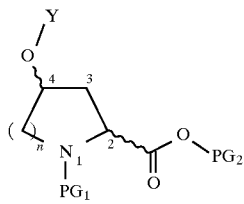

More specifically, Boc-cis- or trans-4-hydroxy-L or D-proline is converted to its allyl ester derivative by treatment with allyl bromide in the presence of a base. The hydroxy group then is alkylated with t-butyl bromoacetate again in the presence of a strong base, preferably NaOH. Next, both the t-butyl-based protecting groups are removed by treatment with TFA. Introduction of the FMOC protecting group by methods known in the art of organic chemistry provides the desired, orthogonally-protected tri-functional scaffold. This scaffold molecule is purified and characterized by methods known in the art of organic synthesis.

In step (2), combinatorial library synthesis using this novel, orthogonally-protected tri-functional scaffold is carried out in several steps. First, equimolar quantities of commercially available resins pre-loaded with protected amino acids are weighed out accurately and mixed together. The resin mixture is deprotected with piperidine in DMF.

In step (3), the resin mixture is treated with an excess of the orthogonally-protected scaffold in sufficient DMF, added together with a suitable coupling reagent and an additive that can be determined by one of skill in the art. The reaction is allowed to take place for a fixed amount of time, and the entire coupling protocol is repeated again or several times, until all the resin has undergone complete conversion to the products. Such conversion can be measured by a variety of methods, including, but not limited to, calorimetric tests (such as ninhydrin test), analytical methods (such as HPLC), and spectroscopic methods (such as $^1$H NMR).

In step (4), the resin mixture is stirred in 50% DCM/DMF and split into an equal number of portions or pools, depending upon the number of carboxylic acids or acid chlorides to be used in the next step.

In step (5), the resin in each pool is deprotected with piperidine in DMF.

In step (6), to the resin in each pool is added a carboxylic acid, an acid chloride, a sulfonyl chloride, an isocyanate, an isothiocyanate, or a chloroformate in a suitable solvent, such as (but not limited to) DMF, DCM, THF or their mixture, in any proportion. Also added is a coupling reagent and/or an additive such as is recognized by a skilled artisan. The reaction is allowed to take place for a fixed amount of time, and the coupling protocol is repeated again or several times, until all the resin has undergone complete conversion to the products.

In step (7), the resin in each pool is taken out and mixed together, and then deprotection of the allyl ester is carried out by known methods.

In step (8), step (4) is repeated, except that the number of equal pools created equals the number of amines to be used in the final step.

In step (9), the resin in each pool is treated with an excess of an amine, a hydrazine, a hydroxylamine or an alcohol in the presence of a known coupling reagent and additive. The reaction is allowed to take place for a fixed amount of time, until all the resin has undergone complete conversion to the products.

In step (10), the resin in each pool is cleaved, either with TFA or a suitable cleavage cocktail containing TFA and scavengers, as may be deemed necessary and as can be determined by a skilled artisan. Alternatively, the resin in each pool is cleaved with boron tribromide in the presence of an alcohol, an amine, a hydrazine or a hydroxylamine.

In step (11), the cleaved products are collected by evaporation of all volatile components in vacuo, and subjected to lyophilization and/or ether precipitation.

In step (12), the products from each pool are dissolved in a sufficient amount of DMSO, and, after appropriate dilutions, screened for various bioactivities.

In step (13), if any pool is found active in any of the screens, it is reiteratively deconvoluted by synthesis and screening of sub-libraries.

In step (14), step (2) is repeated, except, instead of using commercially available pre-loaded amino acid resins, commercially available rink amide resin (or any other commercially available resin appropriate for the synthesis of amides) is used. Each protected amino acid or a protected bifunctional unit can then be loaded onto the rink amide resin in equimolar amounts. Steps (3) to (13) are then carried out as recited above.

Alternatively, Boc-trans-3-hydroxy-L-proline (see below) can also be synthesized and used to generate libraries by similar methods.

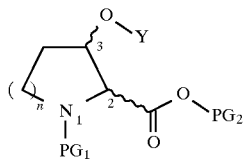

As described above, the methods and reagents of the claimed invention are useful for the generation and deconvolution of peptide and non-peptide chemical combinatorial libraries. These methods and reagents can be advantageously used to obtain libraries of compounds that exhibit a significantly increased magnitude of molecular diversity, as compared to that of combinatorial libraries and compounds currently available in the art.

The invention is further illustrated by the following non-limiting examples.

EXAMPLES

Example 1

Building Block Library One (Amino Acid—Bifunctional Unit—Acid)

Unless otherwise indicated, chemicals were obtained from Sigma Chemical Co., St. Louis, Mo. or from Aldrich Chemical Co., Inc., Milwaukee, Wis.

Resins: Fourteen resin samples (Fmoc-protected amino acids attached to Wang resin (p-benzyloxybenzyl alcohol); Advanced ChemTech, Louisville, Ky. and NovaBiochem, La Jolla, Calif.) were weighed, so that each resin was present at a 0.0625 mmole scale. The details of resins and loadings are described below:

| Amino Acid | Loading (mmoles/cm) | Weight (mg) |
|---|---|---|
| Glycine | 0.72 | 86.8 |
| Leucine | 0.69 | 90.6 |
| Alanine | 0.65 | 96.2 |
| Phenyl Alanine | 0.80 | 78.1 |
| Valine | 0.57 | 109.6 |
| Glutamic Acid | 0.87 | 71.8 |
| Tyrosine | 0.79 | 79.1 |
| Threonine | 0.54 | 115.7 |
| Aspartic Acid | 0.55 | 113.6 |
| Serine | 0.61 | 102.4 |
| D-Valine | 0.57 | 109.6 |
| D-Leucine | 0.76 | 82.2 |
| D-Phenyl Alanine | 0.67 | 93.3 |
| D-Alanine | 0.65 | 96.2 |

These resin samples were combined in a silanized beaker and mixed with 50/50 dimethyl formamide (DMF)/dichloromethane (DCM) for ~2 h. The resin sample mixture was filtered, then rinsed with DMF, then with DCM. The resin was then vacuum dried overnight. Equal portions of the resin mixture (95 mg) were placed into each of 14 wells on an Advanced ChemTech ACT396 MPS (Multi-Peptide Synthesizer). Alternatively, the resin mixture was pipetted from the silanized beaker directly into the Advanced ChemTech 396 MPS as a slurry.

The first step was resin preparation, which involved washing the resin with 1500 µl aliquots of DMF. The resin samples were each washed twice before continuing to the deprotection step. The deprotection step proceeded with an initial washing of the resin samples with 1500 µl of 25% piperidine in DMF for 3 min. This step removed any residual DMF from the wash step. The actual deprotection was carried out for 20 additional min using 1500 µl of 25% piperidine in DMF. The reaction vessel (RVs) were all emptied and washed prior to the coupling step. Each deprotected resin sample was washed first with 1500 µl of fresh DMF. Then each sample was washed 7 times with fresh N-methylpyrolidinone (NMP). This removed all traces of piperidine from the samples. The coupling reactions were carried out using HOBt/PyBOp (bromo-tris-pyrrolidino-phosphonium hexafluorophosphate) chemistry with a 5 min pre-activation step. Alternatively, the coupling reactions were carried out using HOAt/DIC chemistry and triple coupling steps. The bifunctional units (BFu's) that were used are listed below (and represent a 5-fold excess):

| Bifunctional Unit (BFu) | weight (mg) = 0.3125 mmoles |
|---|---|
| 6-Aminocaproic Acid | 109.9 |
| Tic (1,2,3,4-tetrahydro-isoquinoline-3-carboxylic acid) | 124.8 |
| HomoPhenyl Alanine | 124.0 |
| 4-Amino-2-methylcinnamic Acid | 116.8 |
| 2-Napthyl Alanine | 136.7 |
| D-Phenyl Alanine (para-Fluoro) | 126.7 |
| 4-Amino-5-chloro-2-methoxy-benzoic Acid | 125.4 |
| 4-(Aminbomethyl) benzoic Acid | 117.8 |
| N-(4-Aminobenzoyl)-β-Alanine | 124.5 |
| β-Thienyl-L-Alanine | 122.9 |
| 2-(Aminophenylthio) Acetic Acid | 126.4 |
| 3-Aminophenylacetic Acid | 106.7 |
| 4-Aminobutyric Acid | 95.6 |
| trans-4-(aminomethyl)cyclohexane carboxylic Acid | 114.4 |

Coupling reaction: The coupling reaction was performed as follows. HOBt (1.1 g) was dissolved in 2600 µl of DMF. This solution (100 µl; 0.3125 mmoles) was added to each of the above BFu's. PyBOp (4.16 g) was dissolved in 5200 µl of DMF, and 200 µl (0.3125 mmoles) was added to each BFu/HOBt solution. Additional DMF (300 µl) was added to each solution to bring the total volume to 1.0 ml. After waiting 5 min, these solutions were added to the 14 de-protected resin mixture samples on the ACT 396MPS. The coupling reactions were carried out for 1.5 h with mechanical shaking on the synthesizer. After coupling, each of the 14 resin sample mixtures was tested using the standard ninhydrin test for free amines. Because some of the amines were aromatic, their reaction with ninhydrin was examined prior to the actual coupling reaction(s). A negative ninhydrin result is a yellow color, indicating a complete coupling with no free amine present. A blue color indicates a positive ninhydrin result and incomplete coupling. The aromatic BFu's yield either a brown, red or orange color on treatment with ninhydrin (not yellow). This test can therefore be used with non-standard amino acids. After the first coupling, the resins exhibited only two negative results with ninhydrin, indicating that these two couplings were the only ones that were complete. Each BFu was then re-coupled using HOAt/DIC chemistry.

Re-coupling reaction: Each of the above BFu's was re-weighed and dissolved in 300 µl of DMF. HOAt (1-hydroxy-7-azabenzotriazole; 1.19 g) was dissolved in 5.2 m of DMF, and 200 µl (0.3125 mmoles) of this solution was added to each BFu solution. DIC (1,3-diisopropylcarbodiimide; 1.36 g) was dissolved in 2.6 ml of DMF, and 100 µl (0.3125 mmoles) was added to the BFu/HOAt solutions. An additional 400 µl of DMF was added to each, to bring the total volume to 1.0 ml. The reaction was shaken for 2 h. The ninhydrin results from this coupling showed a much larger percentage of BFu's coupling. Six pools were coupled for a third time using the above HOAt/DIC chemistry.

Combined and split procedure: After coupling, 12 of the 14 pools were combined. The two pools removed were: (1) a pool that coupled completely; and (2) a pool that did not couple completely. These samples were saved for further analysis. The remaining 12 pools were combined in 24 ml of a 60:40 mixture of 1,2-dichloroethane/DMF and mixed for 2 h. The resin was split as a slurry, and 950 µl of the mixture was placed into each of 19 wells on the ACT 396MPS using a Rainin Pipetman. This resulted in 60 mg of resin per well (0.0375 mmoles). The resin samples were washed with DMF and de-protected with 25% piperidine, as described above, before coupling with the acid groups.

Final coupling with acid groups: The following acids were used in 3-fold excess for coupling with the resins using HOAt/DIC chemistry:

| Acid group | weight (mg) = 0.1111 mmoles |
|---|---|
| Phenylacetic acid | 24.8 |
| 2-Thiopheneacetic acid | 25.9 |
| 3-Furoic acid | 20.4 |
| Furylacrylic acid | 25.2 |
| 3-(2-thienyl)acrylic acid | 28.1 |
| trans-3-Furanacrylic acid | 25.2 |
| 3-Thiophenecarboxylic acid | 23.4 |
| Coumarin-3-carboxylic acid | 34.7 |
| 5-Methyl-2-thiophenecarboxylic acid | 25.9 |
| 2-Thiopheneglyoxylic acid | 28.5 |
| 2-Oxo-6-pentyl-2H-pyran-3-carboxylic acid | 38.3 |
| Ortho-tolyloxyacetic acid | 30.3 |
| Coumalic acid | 25.5 |
| 2-(para-tolylsulfonyl)-acetic acid | 39.0 |
| 4-(2,4-Dimethylphenyl)butyric acid | 35.0 |
| 4-(2,5-Dimethylphenol)butyric acid | 35.0 |
| 3-(2-Thenoyl)-propionic acid | 33.5 |
| N-Furfurylglutaramic acid | 38.5 |
| 4-chloro-2-(2-thienylethyl)benzoic acid | 48.5 |

The acids were each dissolved in 900 µl of DMF. The above acid groups were prepared for triple couple reactions (three times the list amounts above were actually prepared). HOAt (2.08 g) was dissolved in 15.6 ml of DMF, and 600 µl of this solution was added to each acid solution. An additional 1200 µl of DMF was added to each acid/HOAt solution for a final volume of 2700 µl. Aliquots (900 µl each) of the above solutions were removed and placed into separate vials. To these 19 vials was added 100 µl of DIC solution (2.37 ml DIC in 7.8 ml DMF). These 1.0 ml solutions were added to each of the de-protected resin mixtures (one acid compound for each of the 19 wells containing resin mixtures). The reactions were mixed for 2 h on the ACT 396MPS. After each coupling, the resin samples were washed with fresh DMF solution extensively. This procedure was repeated twice for a total of three couplings. The resins were washed with DCM and the couplings were checked by ninhydrin. All but two of the reactions showed complete coupling, as monitored by ninhydrin.

Cleavage procedure: The compound mixtures were cleaved from the resin using 95% TFE (trifluoroacetic acid)/5% water into 3 ml vials on the ACT 396MPS. Aliquots (1.5 m) of the cleaved solution were added to each well and mixed for 1.5 h. After emptying each reaction vessel, the resin was rinsed with another 1.0 ml of TFA cleavage solution. The TFA was removed by directing a dry nitrogen stream over the sample vials and placing the samples into a vacuum desiccator overnight.

Preparation of deep well titer plates for screening of combinatorial libraries: The dried sample mixtures (168 compounds per well in 17 wells, for a total of 2856 compounds) were dissolved in 500 µl of dimethyl sulfoxide (DMSO). The sample mixtures were transferred to deep well titer plates and dilutions of 1:10 and 1:100 were made for high throughput screening of cell-based assays.

Screening results: The combinatorial chemistry sample pools were subjected to high throughput screening for a determination of biological agonist activity. In these screens, a known bioactive ligand is tested as a positive control in the screening assay, yielding a value termed "Maximum Response." Dilutions of combinatorial chemistry sample pools were tested in the same assay, and resultant values were expressed as "% Maximum Response." Three screening assays identified 4 pools to be further examined. In general, these pools exhibited the highest agonist activity above background that was observed in a given bioassay. For instance, in a calcitonin mimetic screening assay, pool 11 showed a dose-dependent response. This calcitonin bioassay is described in pending patent application U.S. Ser. No. 08/100,887, which is incorporated herein in its entirety.

De-convolution, round one: The 4 pools that were identified in the screening assays were selected for de-convolution (sub-library generation). These sub-libraries represent 14 different resins (combined), 12 different BFu's (separate), and 4 acid compounds (separate). Since the ACT 396MPS is in a 96 well format, all 4 of these sub-libraries were synthesized at once. Each well contained 14 compounds, representing the 14 different resin samples used. The resin samples were prepared as before, but at a 0.03125 mmole scale (50 mg/well).

| Amino Acid | Loading (mmoles/gram) | weight (mg) |
| --- | --- | --- |
| Glycine | 0.72 | 173.6 |
| Leucine | 0.69 | 181.2 |
| Alanine | 0.65 | 192.4 |
| Phenyl Alanine | 0.80 | 156.2 |
| Valine | 0.57 | 219.2 |
| Glutamic Acid | 0.87 | 143.6 |
| Tyrosine | 0.79 | 158.2 |
| Threonine | 0.54 | 231.4 |
| Aspartic Acid | 0.55 | 227.2 |
| Serine | 0.61 | 104.8 |
| D-Valine | 0.57 | 219.2 |
| D-Leucine | 0.76 | 164.4 |
| D-Phenyl Alanine | 0.67 | 186.6 |
| D-Alanine | 0.65 | 192.4 |

The above used an amount of resin such that 1.0 ml of resin solution delivered 0.03125 mmoles (50 mg) per well. The resins were mixed in 51 ml of a 50:50 mixture of DMF/DCM. The slurry was mixed for 2.5 h. Aliquots (950 µl) of this solution were delivered to each well. The synthesis was run using the automatic mode on the ACT 396MPS.

Resin preparation: The resin was washed with 1.0 ml of DMF twice.

Deprotection: One ml of 25% piperidine was added to each well and mixed for 3 min before emptying. An additional 1.0 ml of 25% piperidine in DMF was added and mixed for 20 min to deprotect the amino acids. The deprotected resins were washed 6 times with DMF before the coupling step.

Coupling reaction: N-Methylpyrrolidinone (NMP; 300 µl) was added to each well to fill the void volume of the RV. The 12 BFu's were prepared as follows:

| Bifunctional Unit (BFU) | weight(mg) = 0.156mmoles (5-fold excess) |
| --- | --- |
| 6-Aminocaproic Acid | 876 |
| Tic (1,2,3,4-tetrahydro-isoquinoline-3-carboxylic acid) | 991 |
| HomoPhenyl Alanine | 995 |
| 4-Amino-2-methylcinnamic Acid | 918 |
| 2-Napthyl Alanine | 1085 |
| D-Phenyl Alanine (para-Fluoro) | 1005 |
| 4-Amino-5-chloro-2-methoxy-benzoic Acid | 980 |
| 4-(Aminbomethyl) benzoic Acid | 854 |
| β-Thienyl-L-Alanine | 976 |
| 2-(Aminophenylthio) Acetic Acid | 932 |
| 3-Aminophenylacetic Acid | 853 |
| 4-Aminobutyric Acid | 734 |

A solution of HOBt was prepared by dissolving 9.2 g in NMP to a total volume of 194 ml. Aliquots (8.0 ml) of this solution were added to each BFu above. A 500 µl aliquot of each of these solutions was delivered to the appropriate RVs (0.156 mmoles). DIC solution (250 µl; 0.156 mmoles; prepared by combining 13.4 ml with 124.6 ml NMP) was also added to each RV. The reaction mixtures were shaken for 60 min. The resins were washed with 1.5 ml of NMP prior to additional coupling reactions. This procedure was repeated twice. Ninhydrin tests were conducted, and the samples were all coupled a fourth time for an additional 1.5 h. The synthesis was continued with 3 post-coupling washes with 1.0 ml of DMF before deprotection and coupling with the 4 acid compounds.

Acid couplings: The four different sub-libraries were generated in this final step. The acids were prepared as follows:

| Acid group | weight(mg) = 0.156mmoles |
| --- | --- |
| trans-3-Furanacrylic acid | 856 |
| 2-Oxo-6-pentyl-2H-pyran-3-carboxylic acid | 1303 |
| Coumalic acid | 869 |
| N-Furfurylglutaramic acid | 1308 |

These acids were dissolved in 20 ml of the above HOBt/NMP solution. The same procedure was followed as for the above coupling for BFu's (5-fold excess and triple couple). After running ninhydrin tests, the above acids were coupled a forth time before cleavage.

TFA cleavage: The samples were cleaved from the resin as before on the ACT 396MPS using 95% TFA/5% water. The solutions were dried overnight on a speed vacuum (Savant Instruments, Inc., Farmingdale, N.Y.).

Preparation of deep well titer plates for screen of combinatorial libraries: The dried sample mixtures (14 compounds per well in 48 wells, for a total of 672 compounds) were dissolved in 500 µl of dimethyl sulfoxide (DMSO). The sample mixtures were transferred to the deep well titer plate, and dilutions of 1:10 and 1:100 were made for screening in cell-based assays.

Screening results: When the library of deconvoluted pool 11 was retested in the calcitonin mimetic screening assay, at least two pools displayed agonist activity (pools 9 and 12).

De-convolution, round two: The 2 compound pools that showed activity in the CT assay screen were selected for de-convolution (sub-library generation). These 2 sub-libraries represent 14 different single compounds in 28 wells. The samples were synthesized on the ACT 396MPS. The resin samples were prepared as before, but at a 0.062 mmole scale (100 mg/well).

| Amino Acid | Wells | Loading(mmoles/gram) | weight (mg) |
|---|---|---|---|
| Glycine | 1, 15 | 0.54 | 115 |
| Leucine | 2, 16 | 0.69 | 90 |
| Alanine | 3, 17 | 0.72 | 95 |
| Phenyl Alanine | 4, 18 | 0.80 | 78 |
| Valine | 5, 19 | 0.57 | 109 |
| Glutamic Acid | 6, 20 | 0.87 | 71 |
| Tyrosine | 7, 21 | 0.79 | 78 |
| Threonine | 8, 22 | 0.54 | 115 |
| Aspartic Acid | 9, 23 | 0.55 | 113 |
| Serine | 10, 24 | 0.61 | 102 |
| D-Valine | 11, 25 | 0.57 | 109 |
| D-Leucine | 12, 26 | 0.76 | 82 |
| D-Phenyl Alanine | 13, 27 | 0.67 | 93 |
| D-Alanine | 14, 28 | 0.65 | 95 |

Resin preparation: The resin was washed with 1.0 ml of DMF twice.

Deprotection: Piperidine (25%; 1.5 ml) was added to each well and mixed for 3 min before emptying. An additional 1.5 ml of 25% piperidine in DMF was added and mixed for 20 min to deprotect the amino acids. The deprotected resins were washed 7 times with DMF before the coupling step.

Coupling reaction: N-Methylpyrrolidinone (NMP; 200 μl) was was added to each well to fill the void volume of the RV (reaction vessel). The 2 BFu's were prepared as follows:

Bifunctional Unit (BFu) weight(g)=0.248 mmoles (4-fold excess)

4-Aminobutyric Acid 1.175

β-Thienyl -L-Alanine 1.561

Each BFu was dissolved in 12.0 ml of NMP. Solutions of HATU (5.6 g of HATU was dissolved in NMP to a final volume of 30 ml) and DIEA (22.5 ml of DIEA was combined with 42.5 ml of NMP) were also prepared. The appropriate BFu (750 μl) was added to each RV, and 250 μl of DIEA solution was added to each well. HATU solution (500 μl) was added to complete the reaction mixture. The couple reaction was allowed to proceed for 5.25 h. The resins were then washed 5 times with 1.5 ml portions of NMP. The resin samples were all checked by ninhydrin for completeness of reaction before proceeding to deprotection with 25% piperidine and the final coupling step with the acid group.

Acid couplings: The two different single compound sub-libraries were generated in this final step. The acid was dissolved in 24 ml of the below HOAt solution (6-fold excess). The same procedure was followed as described above for coupling the BFu's (4-fold excess and single couple). After running ninhydrin tests, the above acid was coupled again using HOAt/DIC chemistry before cleavage (e.g., 3.8 g HOAt to a total volume of 49.5 ml in NMP/15.1 ml DIC with 49.9 ml NMP/750 μl acid/HOAt solution added/250 μl DIC/5.25 h coupling).

TFA cleavage: The samples were cleaved from the resin as before on the ACT 396MPS using 95% TFA/5% water. The solutions were dried overnight on a Savant Speed-Vac.

Preparation of dee p well titer plates for screen of combinatorial libraries: The dried samples (28 individual compounds) were dissolved in 500 μl of dimethyl sulfoxide (DMSO). The samples were transferred to the deep well titer plate and dilutions of 1:10 and 1:100 were made for screening in cell based assays.

Screening results: The following pools were tested in the calcitonin mimetic screening assay:

Amino Acid/β-(2-thienyl)Alanine/2-Oxo-6-pentyl-2H-pyran-3-carboxylic acid; and

Amino Acid/4-Aminobutyric Acid/2-Oxo-6-pentyl-2H-pyran-3-carboxylic acid.

Example 3

Building Block Libraries Two and Three

Building block Libraries Two and Three were generated as described in Example 1, except the following sets of components were used.

A. Resin Components

| CL-5 | | CL-6 | |
|---|---|---|---|
| L-Gly | L-Lys | D-Ala | D-Met |
| L-Leu | L-Met | D-Leu | D-Trp |
| L-Ala | L-Trp | D-Phe | D-Asp |
| L-Phe | L-Nle | D-Val | D-Lys |
| L-Val | L-Asn | D-Nle | D-Gln |
| L-Glu | L-Gln | D-Ser | D-His |
| L-Tyr | L-Ile | D-Tyr | |
| L-Thr | L-His | D-Glu | |
| L-Asp | | D-Thr | |
| L-Ser | | D-Asn | |

B. Bifunctional Central Units

6-Aminocaproic Acid

Tic (1,2,3,4-tetrahydroisoquinoline-3-carboxylic acid)

4-Amino-2-chlorobenzoic acid

4-Amino-2-methyl cinnamic acid

2-Napthyl-Ala

D-Phe(pF)

4-Amino-5-chloro-2-methoxy-benzoic acid 4-(Aminomethyl)benzoic acid

Thi (β-Thienyl-L-Ala)

3-Aminobenzoic acid

3-Amino-4-chlorobenzoic acid

4-Aminobutyric acid

4-Aminophenylacetic acid

3-Amino-2,5,-dichlorobenzoic acid

4-Aminobenzoic acid

4-Amino-2-chlorobenzoic acid 4-(4-Aminophenyl)butyric acid 5-(4-Aminobenzamido) valeric acid 11-Aminoundecanoic acid 5-Amino-2-chlorobenzoic acid 4'-Aminooxanilic acid D,L-3-Aminobutyric acid D,L-3-Aminoisobutyric acid Baclofen 8-Aminocaprylic acid 7-Aminoheptanoic acid t-ButylGly β-Ala cyclohexyl-Gly 5-Aminolevalinic acid 12-Aminolauric acid 2-Amino-a-[1-(tert-butoxy-carbonyl)-1-methyl-ethoxyimino]-4-thiazoleacetic acid C. Acid Groups 3-Thiopheneacetic acid 2-Thiopheneacetic acid 3-Thiophenecarboxylic acid 3-(2-Thienyl)acrylic acid trans-3-furanacrylic acid 5-Nitro-2-furoic acid (±)-Tetrahydro-2-furoic acid (R)-(−)-5-oxo-2-tetrahydrofurancarboxylic acid
2-Furoic acid
2-Oxo-6-pentyl-2H-pyran-3-carboxylic acid
trans-3-furanacrylic acid
(S)-(+)-5-oxo-2-tetrahydrofurancarboxylic acid
3-Furoic acid
Coumarin-3-carboxylic acid
Coumalic acid
5,6-Dichloronicotinic acid
3-Rhodaninepropionic acid
6-Methylpicolinic acid
N-Furfurglutaramic acid
N-(2-Thiazolyl)succinamic acid
N-(2-Thiazolyl)glutaramic acid
Gamma-oxo-1-pyrrolidinebutyric acid
ortho-tolyloxyacetic acid
N-(4-methyl-2-pyridyl)succinamic acid
2,4-Dihydroxythiazole-5-acetic acid
N,N-Diethyl-4-sulfamoylbenzoic acid
N-(2-Pyridyl)phthalamic acid
N-(3-Pyridylmethyl)phthalamic acid
1-Methyl-5-oxo-3-pyrrolidinecarboxylic acid
3-(2-Thenoyl)-propionic acid
3-(2-Chlorophenyl)-5-methyl-4-isoxazolecarboxylic acid
1-Benzyl-5-oxo-3-pyrrolidinecarboxylic acid
3,4-Dihydro-2,2-dimethyl-4-oxo-2H-pyran-6-carboxylic acid
4-(2,5-Dimethylphenyl)butyric acid
4-(4-hexadecylphenyl)butyric acid
4-Chloro-2-(2-thienylethyl)benzoic acid
4-(2,4-Dimethylphenyl)butyric acid
5-Phenyl-2-pyrrolepropionic a
2-Thiopheneglyoxylic acid
6-Methylnicotinic acid
(±)-Tetrahydro-3-furic acid
4(-2-Thienyl)butyric acid
N-(6-Methyl-2-pyridylsuccinamic acid
α-Phenylcinnamic acid
2-Methyl-3-furic acid
a-Methyl-2-thiopheneacrylic acid
γ—oxo-2-furanbutyric acid
5-Methyl-3-phenylisoxazole-4-carboxylic acid CL5=18×32×48=27,648 compounds (576 compounds/pool in 48 pools)

CL6=16×32×48=24,576 compounds (512 compounds/pool in 48 pools)

Example 4

Pseudopeptide Library

The following 20 monomers were used to generate a 16,000 compound oxyamide pseudo-tripeptide library:

FMOC-D-α-aminooxy acids (8): OGly, OAla, OVal, OLeu, OIle, OPhe, ONle, ONva.

FMOC-D-α-amino acids (12): Asp(OtBu), Asn, Glu(OtBu), Gln, Pro, Lys(Boc), Orn(Boc), His(Boc), Trp(Boc), Ser(tBu), Thr(tBu), Tyr(tBu).

All 12 FMOC-D-α-amino acids were purchased from Advanced chem Tech (Louisville, Ky.). All 8 FMOC-D-α-aminooxy acids were synthesized according to methods known in the art of organic chemistry (e.g., M. Briggs and J. Morley, *J. Chem. Soc. Perkin* I 2138, 1979; L. Kisfaludy et al., *Acta. Biochem. Biophys.* 6:393, 1971).

A 2.4 mmol quantity of each of the 20 monomers was weighed out and dissolved in 6 ml of dimethylformamide (DMF, Applied Biosystems Inc., Foster City, Calif.).

A 9.6 g (4.8 mmols) quantitiy of Rink Amide MHBA resin (Novabiochem, La Jolla, Calif.) was weighed out and transferred to the collection vessel (CV) of the MPS 357 instrument (Advanced Chem Tech). The resin was robotically split into the 20 reaction vessels (RVs) of the instrument using 78 ml of a 50:50 mixture of dichloromethane (DCM, Applied Biosystems Inc.) and DMF (hereafter referred to as 50% DCM/DMF). The residual resin in the CV was again split into the 20 RVs using another 86 ml of the same solvent. Three more passes were carried out using 78 ml of the same solvent. After these five passes, all the resin had been transferred from the CV to the RVs. The resin in each RV was washed with DMF (3×5 ml).

The resin in each RV was deprotected using 30% piperidine in DMF (5 ml) for 5 min, and then after draining, with another 5 ml of 30% piperidine (Advanced Chem Tech) in DMF for 25 min. The resin in each RV was washed with DMF (9×5 ml). The resin in each RV was coupled to a monomer using a 5-fold excess of the monomer (1.2 mmols) in DMF (5 ml) in the presence of coupling reagents 1-hydroxy-7-azabenzotriazolyluronium hexafluorophosphate (HATU; PerSeptive Biosystems, Framingham, Mass.; 1.2 mmols), 1-hydroxy-7-azabenzotriazole (HOAT; PerSeptive Biosystems; 1.2 mmols) and diisopropylethylamine (DIEA, Advanced Chem Tech; 2.4 mmols). The coupling was carried out by mixing for 4 h, and then the solvents were drained and the resin washed with DMF (6×5 ml). At this time, a ninhydrin test of the resin in each of the 20 RVs was carried out, and essentially showed the coupling to be complete.

A one-third portion of the resin in each RV was saved for future analysis or for use in deconvolution, if so needed. The remaining two-thirds of the resin in each RV was robotically combined to the CV by robotically pipetting 3.5 ml of 50% DCM/DMF into each RV and transferring the entire amount to the CV. This operation was repeated six more times to ensure complete transfer of the resin from the RVs to the CV.

The resin in the CV was then robotically split into the 20 reaction vessels (RVs) of the instrument using 82 ml of 50% DCM/DMF. The residual resin in the CV was again split into the 20 RVs using another 87 ml of the same solvent. Three more passes were carried out using 78 ml of the same solvent. After these five passes, all the resin had been transferred from the CV to the RVs. The resin in each RV was washed with DMF (3×5 ml).

The resin in each RV was deprotected using 30% piperidine in DMF (3.5 ml) for 5 min, and then after draining, with another 3.5 ml of 30% piperidine in DMF for 25 min. The resin in each RV was washed with DMF (9×3 ml). The resin in each RV was coupled to a monomer using a 5-fold excess of the monomer (0.8 mmols) in DMF (3 ml) in the presence of coupling reagents HATU (0.8 mmols), HOAT (0.8 mmols), and DIEA (1.6 mmols). The coupling was carried out by mixing for 4 h, and then the solvents were drained and the resin washed with DMF (6×5 ml). At this time, a ninhydrin test of the resin in each of the 20 RVs was carried out and essentially showed the coupling to be complete. A one-half portion of the resin in each RV was saved for future analysis or use in deconvolution, if so needed. The remaining one-half of the resin in each RV was robotically combined to the CV by robotically pipetting 3.5 ml of 50% DCM/DMF into each RV and transferring the entire amount to the CV. This operation was repeated six more times to ensure complete transfer of the resin from the RVs to the CV.

The resin in the CV was then manually split into the 40 reaction vessels (RVs) of the MPS 396 instrument using 42 ml of 50% DCM/DMF. The residual resin in the CV was again split into the 20 RVs using another 40 ml of the same solvent. After these two passes, all the resin had been transferred from the CV to the RVs. The resin in each RV was washed with DMF (3×1 ml).

The resin in each RV was deprotected using 30% piperidine in DMF (1 ml) for 5 min, and then after draining, with another 1 ml of 30% piperidine in DMF for 25 min. The resin in each RV was washed with DMF (9×1 ml). The resin in each of the first 20 RVs was coupled to a monomer using a 5-fold excess of the monomer (0.8 mmols) in DMF (1 ml) in the presence of coupling reagents HATU (0.2 mmols), HOAT (0.2 mmols), and DIEA (0.4 mmols). The resin in each of the next 20 RVs was coupled to a monomer in the same way. The coupling was carried out by mixing for 4 h, and then the solvents were drained and the resin washed with DMF (6×1 ml). At this time, a ninhydrin test of the resin in each of the 20 RVs was carried out, and essentially showed the coupling to be complete.

The resin in each RV was deprotected using 30% piperidine in DMF (1 ml) for 5 min, and then after draining, with another 1 ml of 30% piperidine in DMF for 25 min. The resin in each RV was washed with DMF (9×1 ml). The resin in each of the first 20 RVs was acylated with acetic anhydride (Advanced Chem Tech) using a solution of the anhydride (0.5M) in DMF (1 ml) in the presence of coupling HOAT (0.5M) and DIEA (0.125M). The resin in each of the next 20 RVs was left free. The acylation was carried out by mixing for 4 h, and then the solvents were drained and the resin washed with DMF (9×1 ml). The resin in all of the RVs was washed with 50% DCM/MeOH (6×1 ml), and then dried in vacuo for 2 h.

Cleavage of the resin in each RV was carried out by adding 1.5 ml of the cleavage reagent (95% TFA (Fluka, Ronkonkoma, N.Y.) and 5% $H_2O$), mixing for 3 h, and then filtering the solutions separately from each RV into each of 40 vials. The resin in each RV was washed with a further 1 ml of the cleavage reagent for 5 min, and the solutions were again filtered into the same set of 40 vials. The filtrates in the 40 vials were transferred to a Savant speed vacuum, and evaporated in vacuo overnight. To the residue in each vial was added 1 ml of water, and it was vortexed for 1 min. The contents of each vial were lyophilized overnight.

The crude residue in each vial was dissolved in 400 $\mu$l of DMSO (Aldrich) by vortexing for a few minutes, and then 200 $\mu$l was precipitated onto a microtiter plate. A 1:10 and a 1:100 dilution of each of the 40 samples was carried out also on the same microtiter plate, and the plate was submitted for high throughput screening. Based on the initial loading of the resin, and assuming 100% yields in each coupling and in cleavage, the final assay concentrations (after a final 1:100 dilution in water of each of the three dilutions of each of the 40 samples) were estimated to be 1000 $\mu$M, 100 $\mu$M and 10 $\mu$M for the three dilutions of each sample.

The entire library generated comprised 16,000 compounds in 40 pools of 400 compounds each.

In a PDGF inhibitor screen, several pools showed high inhibitory activity at the top concentration of 1000 $\mu$M, but at the next lower concentration of 100 $\mu$M, only a few pools showed potent inhibitor activity only one of the pools yielded greater than 50% inhibition of PDGF. This pool is subjected to iterative deconvolution to identify a single active compound as a lead.

Example 5

Synthesis of N-FMOC-2-allyloxycarbonyl-pyrrolidine-4-oxyacetic acid as an Orthogonally-Protected Tri-functional Scaffold Boc-trans-4-hydroxy-L-proline (Novabiochem, La Jolla, Calif.; 23.1 g, 100 mmols), diisopropylethylamine (Advanced Chem Tech; 13 g, 100 mmols), and allyl bromide (Aldrich; 24 g, 200 mmols) were dissolved in 500 ml of ethyl acetate (EM Science, Gibbstown, N.J.). The mixture was refluxed overnight, and was then cooled to room temperature (RT). This mixture was washed first with water, and then with 500 ml of 5% aqueous sodium bicarbonate (Mallinckrodt, Paris, Ky.) to remove unreacted starting material. The organic layer was then washed with water and brine, dried over anhydrous $MgSO_4$ (Sigma), and filtered. The filtrate was concentrated in vacuo to a pale yellow oil, which was dried in vacuo overnight.

The crude product was dissolved in 500 ml of dry tetrahydrofuran (THF; Aldrich) and stirred under $N_2$ in an ice bath. Sodium hydride (Aldrich; 2.5 g, 62.5 mmols) was added, and the mixture was stirred for 15 min. Then 18-crown-6 (Aldrich; 13 g, 50 mmols) and t-butyl bromoacetate (Aldrich; 12.2 g, 62.5 mmols) were added, and the mixture was stirred at RT overnight. It was then concentrated in vacuo, and the residue was partitioned between water and ethyl acetate. The organic layer was drawn off, washed with water, brine, dried over anhydrous $MgSO_4$, filtered, and the filtrate was concentrated in vacuo to a tan oil.

The crude product was dissolved in 100 ml of trifluoroacetic acid (Aldrich) and stirred at RT under $N_2$ for 3 h. It was then concentrated in vacuo to a pale yellow semi-solid.

The crude product was taken into 400 ml of a 1:1 mixture of acetone (EM Science) and water. Sodium carbonate (Mallinckrodt; 10.6 g, 100 mmols) was added, followed by FMOC-OSu (Advanced Chem: Tech16,.85 g, 50 mmols). The mixture was stirred at RT overnight, and then concentrated in vacuo to remove the acetone. The residual aqueous solution was diluted further with 300 ml of water, and extracted with ethyl acetate twice. The organic layers were discarded. The aqueous layer was acidified to pH 3 with 3N HCl and extracted twice with ethyl acetate. The combined organic extracts were washed with water, brine, and dried over anhydrous $MgSO_4$. It was then filtered and concentrated in vacuo to a pale yellow oil. Purification by flash column chromatography on a silica gel column, and elution with a gradient of 0–5% of DCM/MeOH gave the pure product, which was dried in vacuo overnight, yielding 15.8 g of a glassy solid (overall yield 35% from Boc-trans-4-hydroxy-L-proline). The product showed a single spot on silica gel thin layer chromatography plates (solvent system: 5% MeOH in DCM). $^1H$ NMR spectra showed signals consistent with the structure of the product.

Example 6

Synthesis of a Peptidomimetic Combinatorial Library using N-FMOC-2-allyloxycarbonyl-pyrrolidine-4 -oxyacetic acid as an Orthogonally-Protected Tri-functional Scaffold Using commercially available 20 L-amino acid Wang resins, a diverse set of 20 carboxylic acid chlorides, and a diverse set of 20 amines (as listed below; Aldrich), a peptidomimetic combinatorial library of 8000 compounds was synthesized.

A 0.06 mmol quantity of each of the 20 L-amino acid Wang resins was weighed out and transferred to a 100 ml flask previously silanized and air dried. The resin mixture was deprotected with 50 ml of 25% piperidine in DMF for 45 min, drained, and the resin washed with DMF (6×25 ml), followed by DCM (4×25 ml).

The resin was coupled to the scaffold using a 5-fold excess of the scaffold (6 mmols), diisopropylcarbodiimide (DIC; Fluka, Ronkonkoma, N.Y.; 6 mmols) and HOAT (6 mmols). The resin was mixed with the coupling mixture for 4 h, drained, and washed with DMF (4×25 ml), followed by DCM (4×25 ml). At this time, a ninhydrin test of a small resin sample showed complete coupling.

The resin was deprotected with 50 ml of 25% piperidine in DMF for 45 min, drained, and washed with DMF (6×25 ml), followed by DCM (4×25 ml), and dried overnight in vacuo.

The resin was split up into 20 pools, and to the resin in each pool was added a 10-fold excess of an acid chloride (0.6 mmols) and a 5-fold excess of 4-dimethylaminopyridine (DMAP; Fluka; 0.3 mmols) in 2 mL of DCM. The resin in each pool was mixed overnight and then drained and washed with DCM (6×2 mL) and DMF (6×2 mL). At this time, a ninhydrin test of a small resin sample showed complete coupling.

The resin from each pool was mixed together by being transferred to a 100 ml flask previously silanized and air dried. The allyl ester was deprotected with tetrakis (triphenylphosphine) palladium (Aldrich; 90 mg) in a mixture of 50 ml of THF and 5 ml of morphine. The resin was mixed at RT overnight, drained, washed with DMF (4×25 ml) and DCM (4×25 ml), and air dried overnight.

The resin was split up into 20 pools, and to each pool was added a 5-fold excess of DIC (0.3 mmols) and HOAT (0.3 mmols) in 1 ml of DMF. The resin in each pool was mixed for 2 h, and then to each pool was added a 10-fold excess of an amine (0.6 mmols) in 1 ml of DMF. The resin in each pool was mixed overnight, drained, and washed with DMF (6×2 ml) and DCM (6×2 ml), and then dried in vacuo overnight.

The resin in each pool was cleaved with 5 ml of Reagent K (90 ml TFA, 5 ml water, 5 m ethanedithiol (Fluka), 2.5 ml thioanisole (Aldrich), and 7.5 g phenol (Fluka)) by stirring for 3 h at RT, and the solutions were collected by filtration in vials. The resin in each pool was washed with 1 ml of TFA and 1 ml of DCM, and the washings from each pool were added to the respective filtrates from each pool. The combined filtrates and washings were concentrated in vacuo on a Savant speed vacuum overnight. To the residue in each vial as added 3 ml of cold dry ether (EM Science), and the suspension was vortexed for a few minutes to obtain a white recipitate. The precipitates were allowed to settle, the supernatents were decanted, and the precipitates in each vial were again treated with ether, as above, and again collected by decantation. The precipitates were dried in vacuo overnight.

The solids in each vial were dissolved in 200 ul of DMSO (Aldrich) by vortexing for a few minutes, and then were pipetted into a microtiter plate. A 1:10 and a 1:100 dilution of each of the 20 samples was also added to the same microtiter plate, and the plate was submitted for high throughput screening. Based on the initial loading of the resin, and assuming 100% yields in each coupling and in cleavage, the final assay concentrations (after a final 1:100 dilution in water of each of the three dilutions of each of the 40 samples) were estimated to be 2000 $\mu$M, 200 $\mu$M and 20 $\mu$M for the three dilutions of each sample.

The entire library generated comprised 8000 compounds in 20 pools of 400 compounds each.

In the calcitonin mimetic screen (CT mimetic screen), several pools showed high CT mimetic activity at the concentration of 200 $\mu$M. When the screening was repeated at pool concentrations of 125 $\mu$M and 62.5 $\mu$M, only a few pools showed potent CT mimetic activity. One of the pools yielded greater than 65% CT mimetic activity at a pool concentration of 125 $\mu$M. This pool is iteratively deconvoluted to obtain a single active compound as a lead.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A combinatorial library of non-peptide compounds comprising a plurality of compounds of the formula:

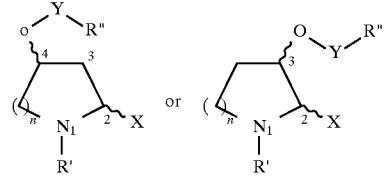

wherein

X is COR, COR" or NHCOR";

Y is CO, $CH_2CO$, $CH_2SO_2$, $CH_2PO_2R$, $CH_2Ph$—CO, $CH_2Ph$—$SO_2$ or $CH_2Ph$—PO $_2R$;

R is H or a substituted or unsubstituted alkyl, cycloalkyl, aryl, arylalkyl, heteroaryl, or heteroarylalkyl; and R' is COR, $SO_2R$, $PO_2R_2$, $CONR_2$, $CSNR_2$, or COOR;

R" is OR, $NR_2$, $N(R)NR_2$ or N (R)OR; and n is 1 or 2.

2. The combinatorial library of claim 1, wherein stereochemistry at $C_2$ and $C_4$ is RR, RS, SR, or SS.

3. The combinatorial library of claim 1, wherein at least one of R, R' and R" has at least one chiral center.

* * * * *